(12) United States Patent
Herzberg

(10) Patent No.: US 7,837,642 B2
(45) Date of Patent: Nov. 23, 2010

(54) KNEE IMMOBILIZER

(75) Inventor: Thorsten Herzberg, Henstedt-Ulzburg (DE)

(73) Assignee: BSN medical GmbH, Hamburg (DE)

( * ) Notice: Subject to any disclaimer, the term of this patent is extended or adjusted under 35 U.S.C. 154(b) by 141 days.

(21) Appl. No.: 11/914,006

(22) PCT Filed: May 9, 2005

(86) PCT No.: PCT/IB2005/001488

§ 371 (c)(1),
(2), (4) Date: Sep. 29, 2008

(87) PCT Pub. No.: WO2006/120498

PCT Pub. Date: Nov. 16, 2006

(65) Prior Publication Data

US 2009/0216166 A1 Aug. 27, 2009

(51) Int. Cl.
*A61F 5/00* (2006.01)
(52) U.S. Cl. .................... 602/26; 602/5; 602/23
(58) Field of Classification Search .......... 602/5, 602/23, 26; 128/869, 882; 2/2
See application file for complete search history.

(56) References Cited

U.S. PATENT DOCUMENTS

| | | |
|---|---|---|
| 4,041,940 A | 8/1977 | Frankel et al. |
| 4,111,194 A | 9/1978 | Cox et al. |
| 4,217,893 A | 8/1980 | Payton |
| 4,349,016 A | 9/1982 | Glassman et al. |
| 4,996,979 A | 3/1991 | Grim et al. |
| 5,387,185 A | 2/1995 | Johnson, Jr. et al. |

FOREIGN PATENT DOCUMENTS

| | | |
|---|---|---|
| EP | 0067319 A | 12/1982 |
| FR | 2740027 A | 4/1997 |

*Primary Examiner*—Patricia M Bianco
*Assistant Examiner*—Camtu T Nguyen
(74) *Attorney, Agent, or Firm*—Adams Intellectual Property Law

(57) ABSTRACT

A knee immobilizer (10) including an elongate frame (12) having opposed convex and concave major surfaces for being positioned along a longitudinal axis of a dorsal aspect of a leg from above to below the knee, and a plurality of outwardly-extending retainers (12A-12D, 12E-12G) cooperating with the frame (12) for retaining the frame (12) on the leg. A lining (16) is provided for being positioned between the frame (12) and the leg when in use to cushion and protect the leg against direct contact with the frame (12). A spine (18) is provided for being positioned on the frame (12) substantially along an elongate axis of the frame (12) from above to below the knee and formed in an angle for maintaining the frame (12) in a predetermined rigid medical treatment extension position on the leg.

6 Claims, 6 Drawing Sheets

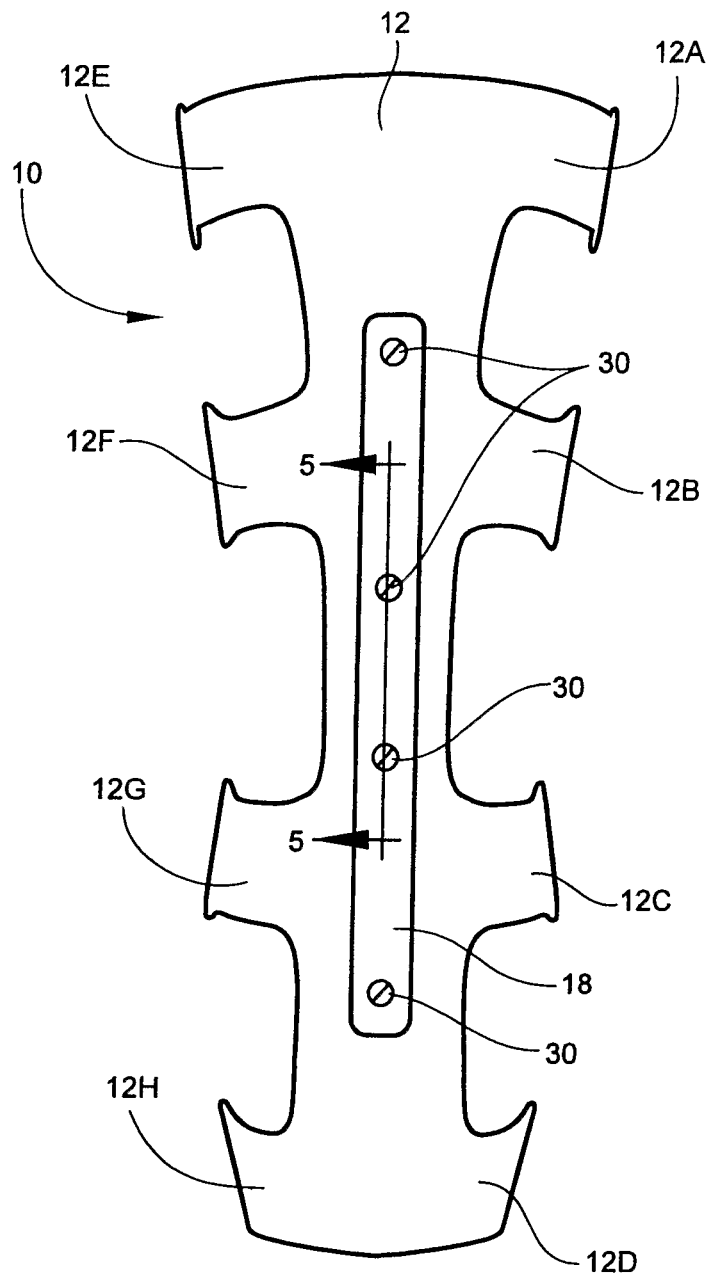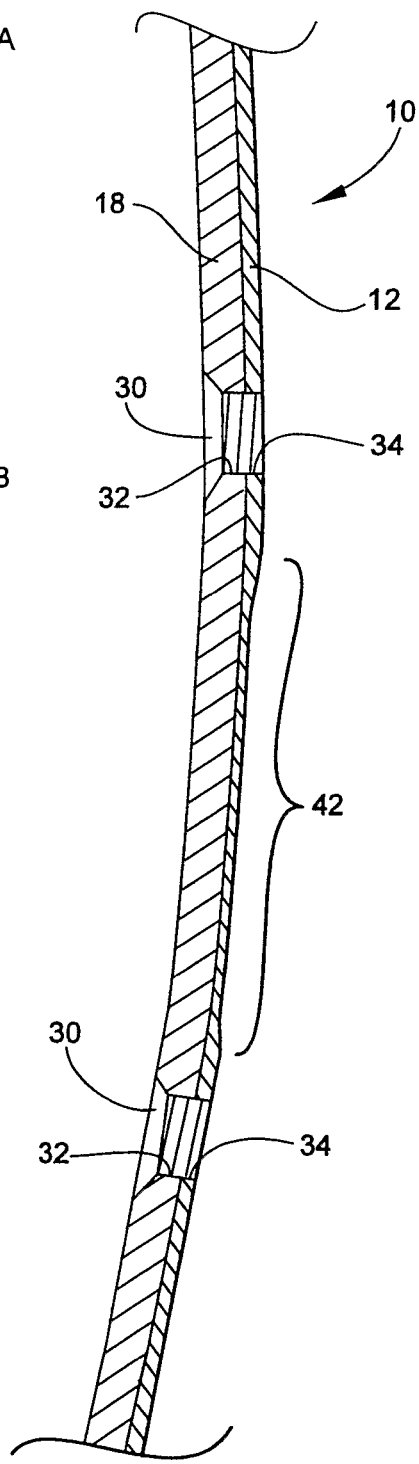
Fig. 4
Fig. 5

KNEE IMMOBILIZER

TECHNICAL FIELD AND BACKGROUND OF THE INVENTION

This invention relates to a knee immobilizer characterized by being adaptable to being positioned on the leg of a patient so as to maintain the leg either in full extension or in light flexion. The knee immobilizer is lightweight and easy to apply to and remove from the leg, while nevertheless providing the required immobilization.

Knee Immobilization is indicated for conservative treatment after recent PCL-rupture, postoperative treatment after PCL surgery or reconstruction, temporary immobilization after knee TEP, patella luxation, ligament rupture, meniscus injuries and patellar tendon rupture.

Significant clinical support exists for the desirability of knee immobilization after injury or surgery, as indicated above. In many instances, "light flexion" is desirable to hold the knee is a slightly flexed position in order to reduce stress on the ligaments and tendons. In general, knee flexion angle of about 20 degrees is considered appropriate in most cases, both from a treatment and patient comfort perspective.

SUMMARY OF THE INVENTION

Therefore, it is an object of the invention to provide a knee immobilizer that allows positioning of the knee in either a full extension or predetermined flexion position.

It is another object of the invention to provide a knee immobilizer that is lightweight.

It is another object of the invention to provide a knee immobilizer that is usable on either the left or right leg.

These and other objects of the present invention are achieved in the preferred embodiments disclosed below by providing a knee immobilizer, comprising, an elongate frame having opposed convex and concave major surfaces for being positioned along a longitudinal axis of a dorsal aspect of a leg from above to below the knee, and a plurality of outwardly-extending retainers cooperating with the frame for retaining the frame on the leg. A lining is provided for being positioned between the frame and the leg when in use to cushion and protect the leg against direct contact with the frame, and a spine is adapted for being positioned on the frame substantially along an elongate axis of the frame from above to below the knee and formed in an angle for maintaining the frame in a predetermined rigid extension position on the leg.

According to one preferred embodiment of the invention, the retainers comprise opposed lateral extensions from the frame for being positioned on respective lateral and medial aspects of the leg.

According to another preferred embodiment of the invention, the retainers comprise a plurality of opposed lateral extensions integrally-formed with the frame and for being positioned on respective lateral and medial aspects of the leg, and slots formed in respective end portions of the lateral extensions to receive adjustable straps for encircling the leg and maintaining the frame in an immobilizing position against the dorsal aspect of the leg.

According to yet another preferred embodiment of the invention, the frame includes a plurality of longitudinally spaced-apart attachment members for releasably retaining the spine.

According to yet another preferred embodiment of the invention, the knee immobilizer includes first and second rigid spines, the first spine having a first predetermined angle of flexion for attaching to and holding the frame in a first corresponding degree of flexion, and the second spine having a second predetermined angle of flexion for holding the frame in a second corresponding degree of flexion, both first and second spines being adapted for being releasably attached to the frame.

Preferably, the lining comprises a spacer fabric.

According to yet another preferred embodiment of the invention, the frame is molded of a semirigid plastic material.

According to yet another preferred embodiment of the invention, the attachment members comprise complementary screws positioned on the spine and threaded screw holes in the frame.

According to yet another preferred embodiment of the invention, the concave surface of the frame includes attachment means for securing the lining to the frame.

According to yet another preferred embodiment of the invention, the frame includes a flexible zone positionable behind the knee for allowing the frame to conform to the angle of the spine.

According to yet another preferred embodiment of the invention, the flexible zone comprises an area of decreased thickness extending transversely across the width of the frame.

According to yet another preferred embodiment of the invention, the knee immobilizer includes an elongate semirigid frame having opposed convex and concave major surfaces for being positioned along a longitudinal axis of a dorsal aspect of a leg from above to below the knee and strap means cooperating with the frame for encircling and retaining the frame on the leg. A spacer lining is provided for being positioned between the frame and the leg when in use to cushion and protect the leg against direct contact with the frame. A first rigid spine is provided and is adapted for being positioned on the frame along an elongate axis of the frame from above to below the knee in alignment with the longitudinal axis of the leg for maintaining the frame in a first predetermined rigid medical treatment extension position on the leg. A second rigid spine is adapted for being positioned on the frame along an elongate axis of the frame from above to below the knee in alignment with the longitudinal axis of the leg for maintaining the frame in a second predetermined rigid medical treatment extension position on the leg in substitution for the first rigid spine.

According to yet another preferred embodiment of the invention, the first spine is formed to an angle whereby the knee is immobilized in a position of less than 10 degrees s of flexion, and the second spine is formed to an angle whereby the knee is immobilized in a position of between about 10 degrees and about 30 degrees flexion.

According to yet another preferred embodiment of the invention, the first and second spines are formed from one or more materials selected from the group consisting of plastic, metal, carbon fiber, and glass fiber.

According to yet another preferred embodiment of the invention, the strap means comprise a plurality of opposed straps integrally-formed with the frame and adapted to receive respective flexible straps for extending across a ventral aspect of the leg.

According to yet another preferred embodiment of the invention, the frame is formed of a thermoplastic material.

According to yet another preferred embodiment of the invention, the spacer lining includes a velour facing fabric laminated to a liner backing.

According to yet another preferred embodiment of the invention, the spacer lining is fabricated from one or more materials selected from the group consisting of velour fabric, toweling fabric, open cell foam, closed cell foam, nylon fabric, and polypropylene fabric.

According to yet another preferred embodiment of the invention, the frame is symmetrical from side to side and adapted for use on both a left and right leg.

BRIEF DESCRIPTION OF THE DRAWINGS

Some of the objects of the invention have been set forth above. Other objects and advantages of the invention will appear as the invention proceeds when taken in conjunction with the following drawings, in which:

FIG. 4 is a dorsal view elevation of the knee immobilizer showing placement and attachment of the spine;

FIG. 5 is a vertical cross-sectional view of the knee immobilizer taken along lines 5-5 of FIG. 4;

DESCRIPTION OF THE PREFERRED EMBODIMENT AND BEST MODE

Figure 1:
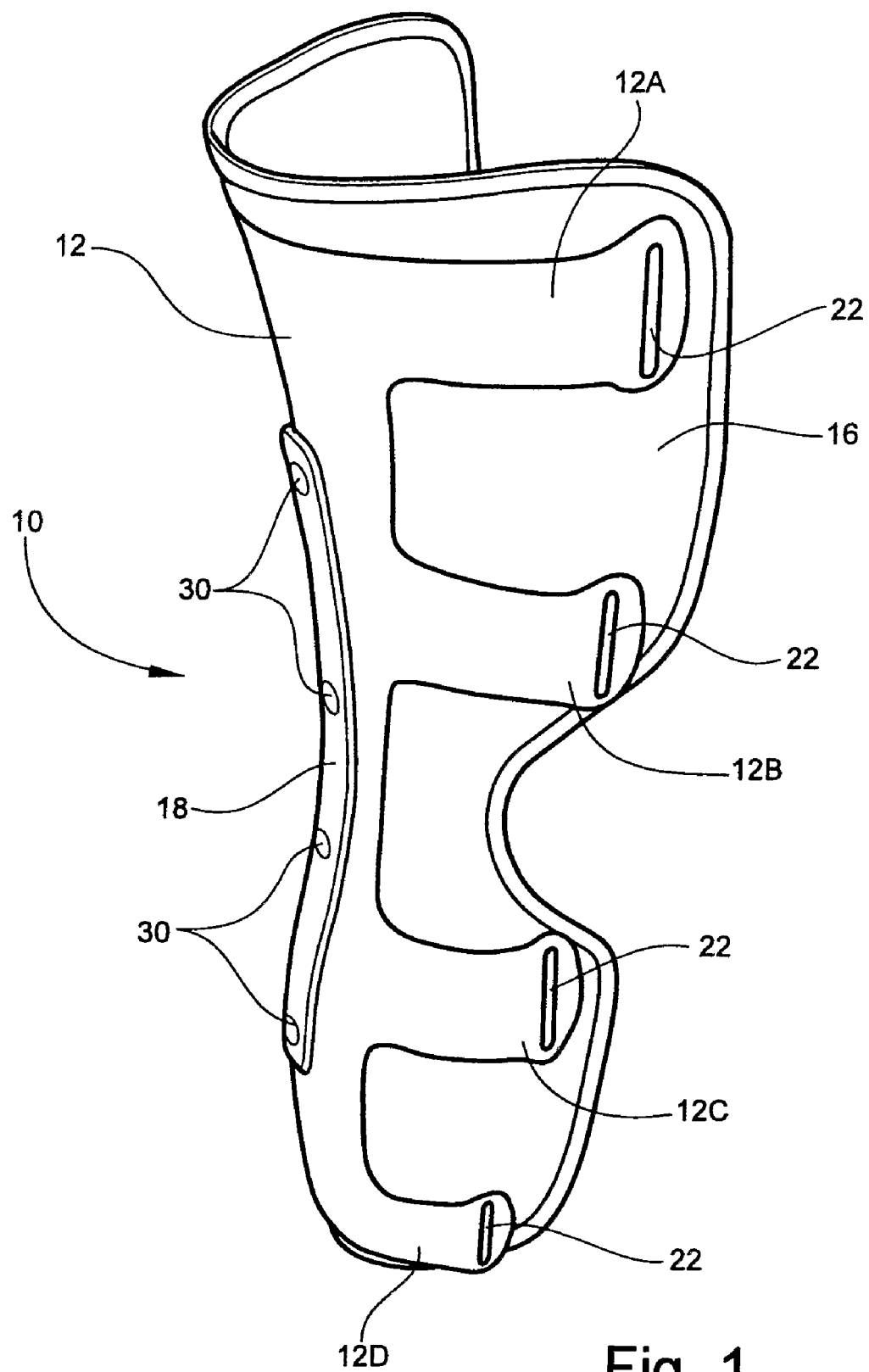
FIG. 1 is a perspective view of a knee immobilizer according to a preferred embodiment of the invention.
Figure 2:
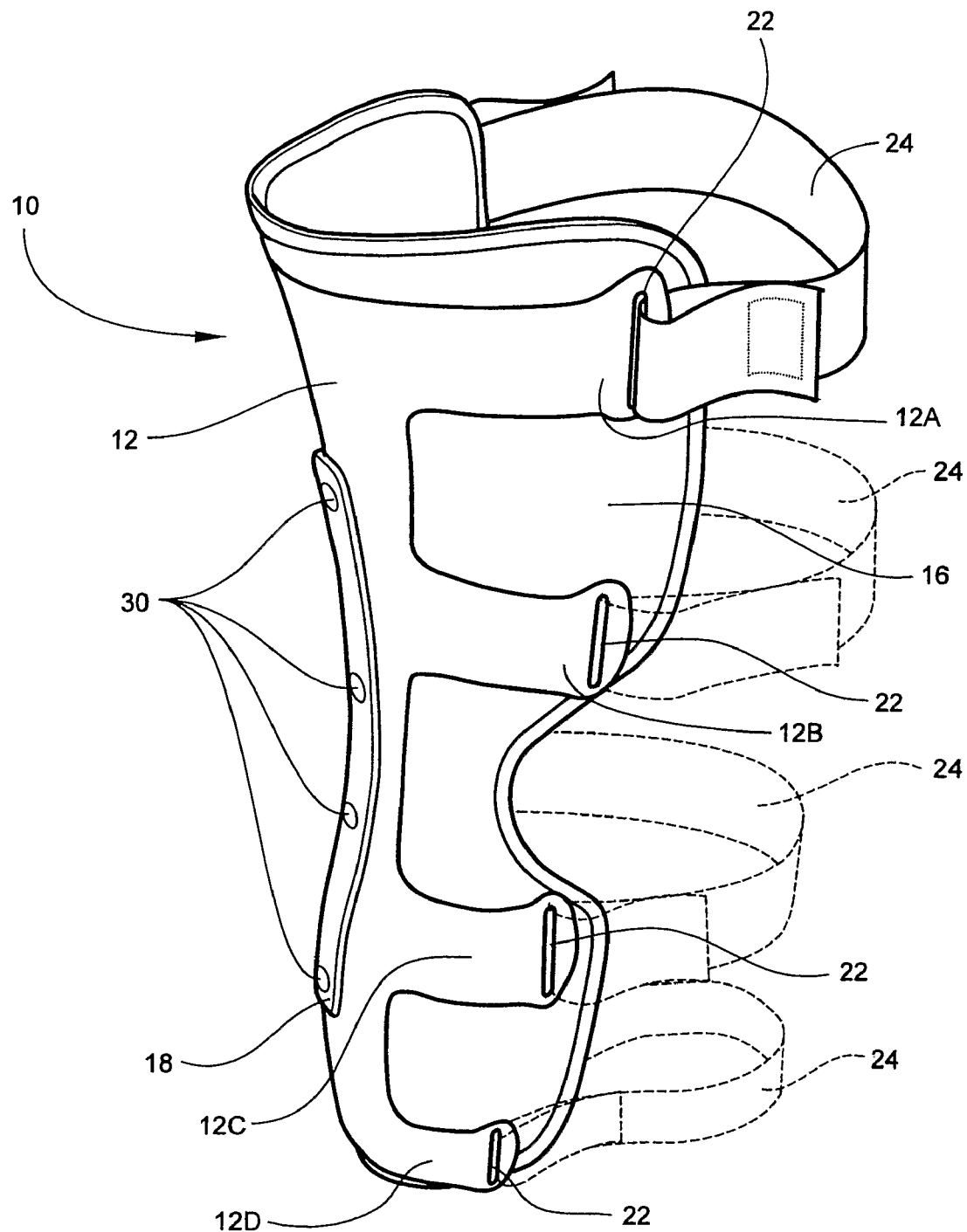
FIG. 2 is a perspective view of the knee immobilizer of FIG. 1 with attached fastening straps.
Figure 3:
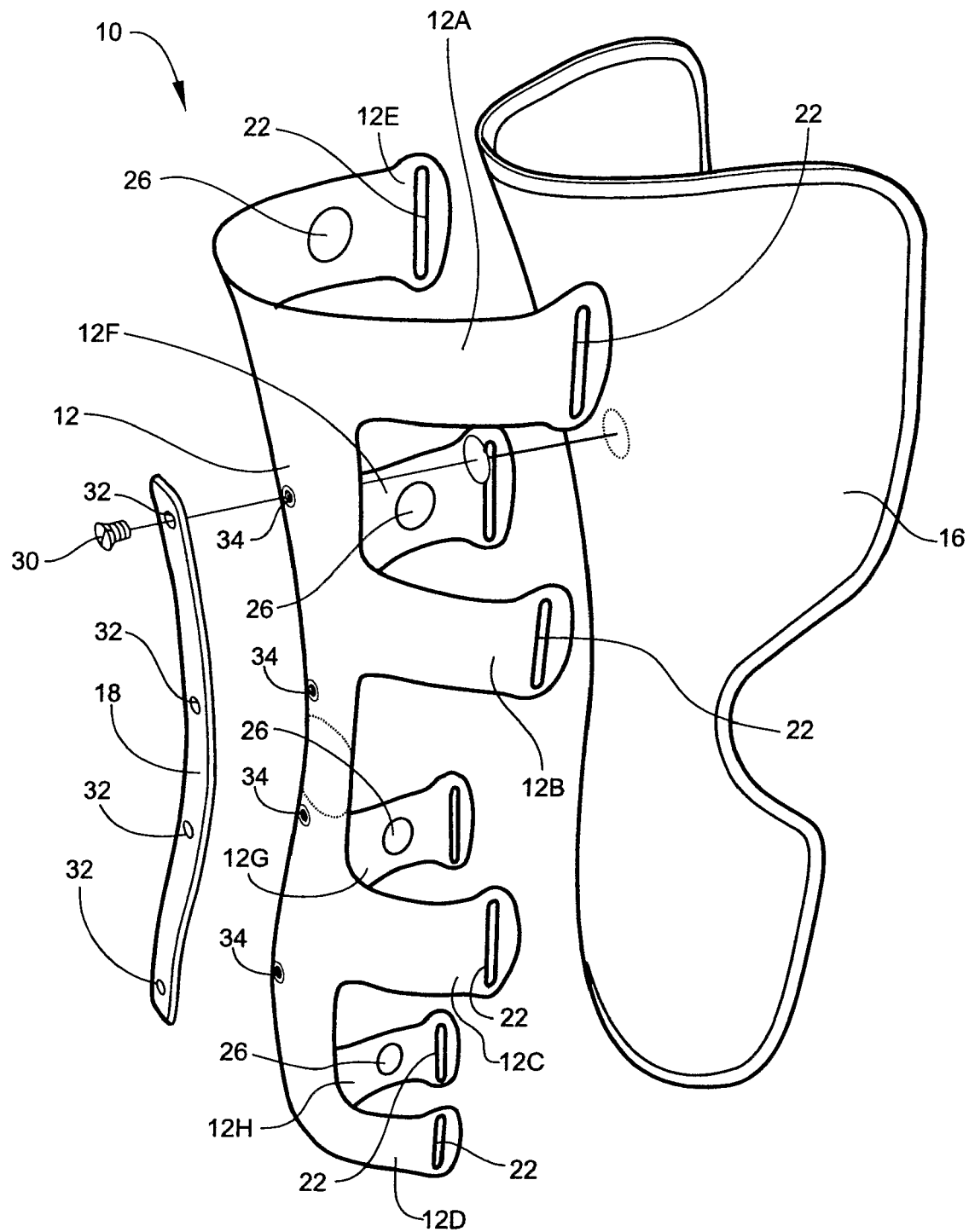
FIG. 3 is an exploded perspective view of the knee immobilizer of FIG. 1.
Figure 6:
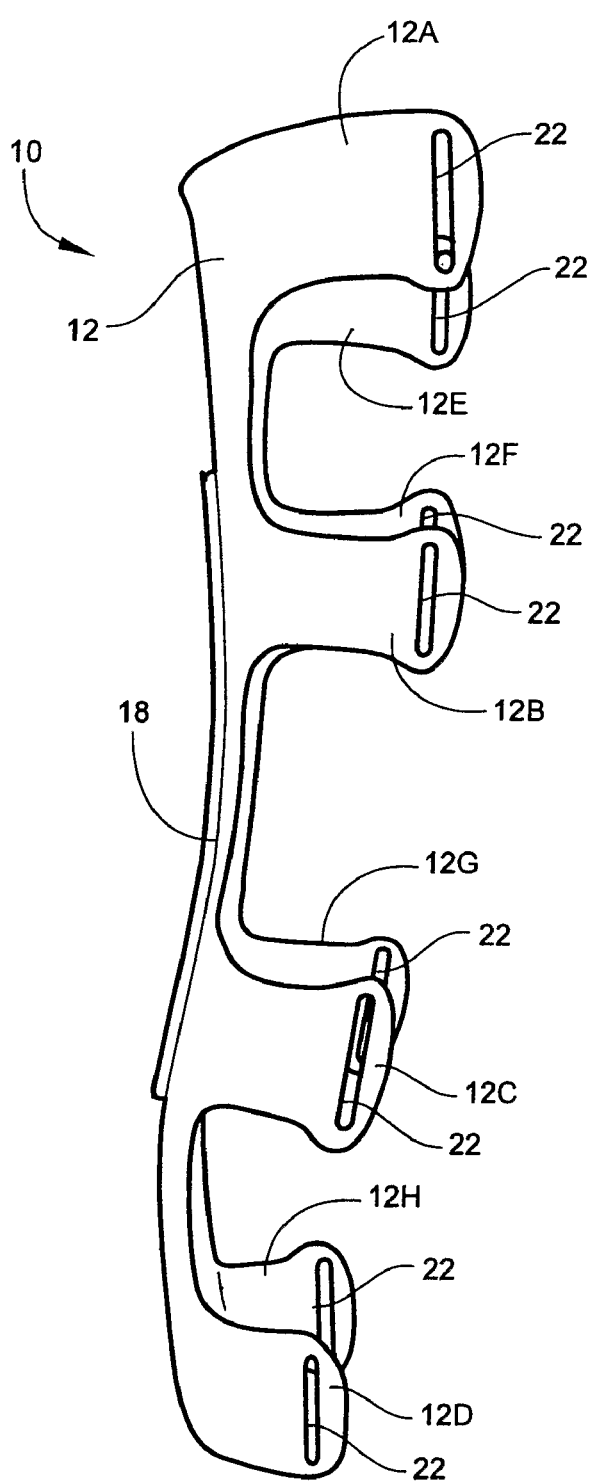
FIG. 6 is a side elevation of a knee immobilizer in a full extension position.
Figure 7:
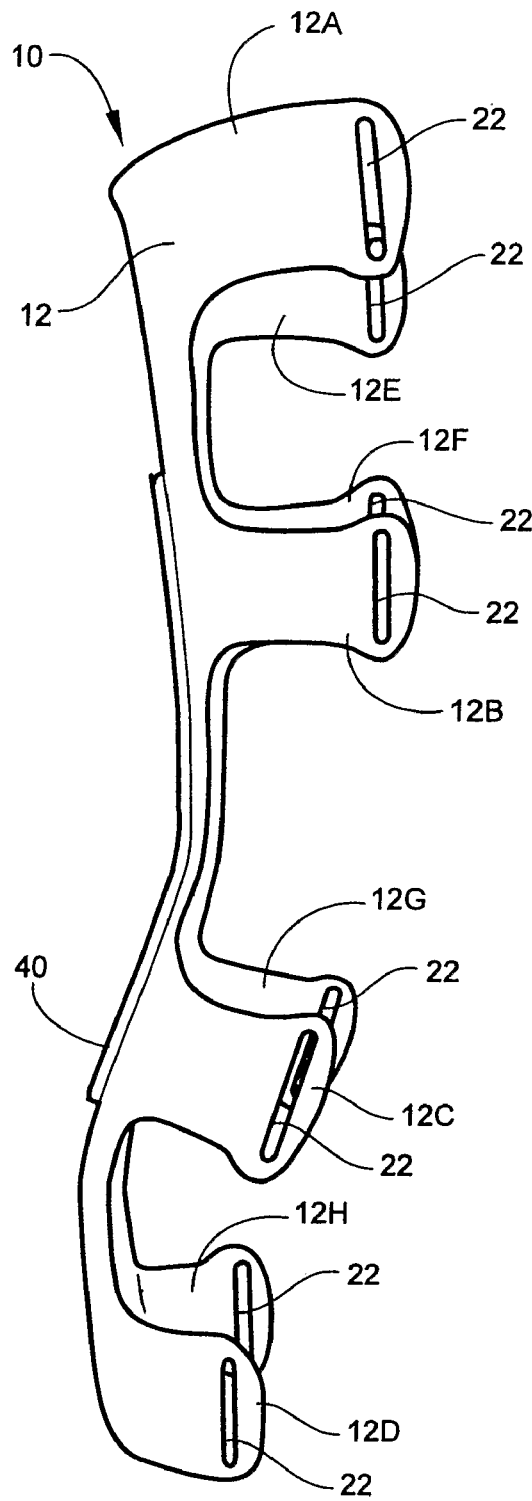
FIG. 7 is a side elevation of a knee immobilizer in a flexion position.
Figures 8, 9:
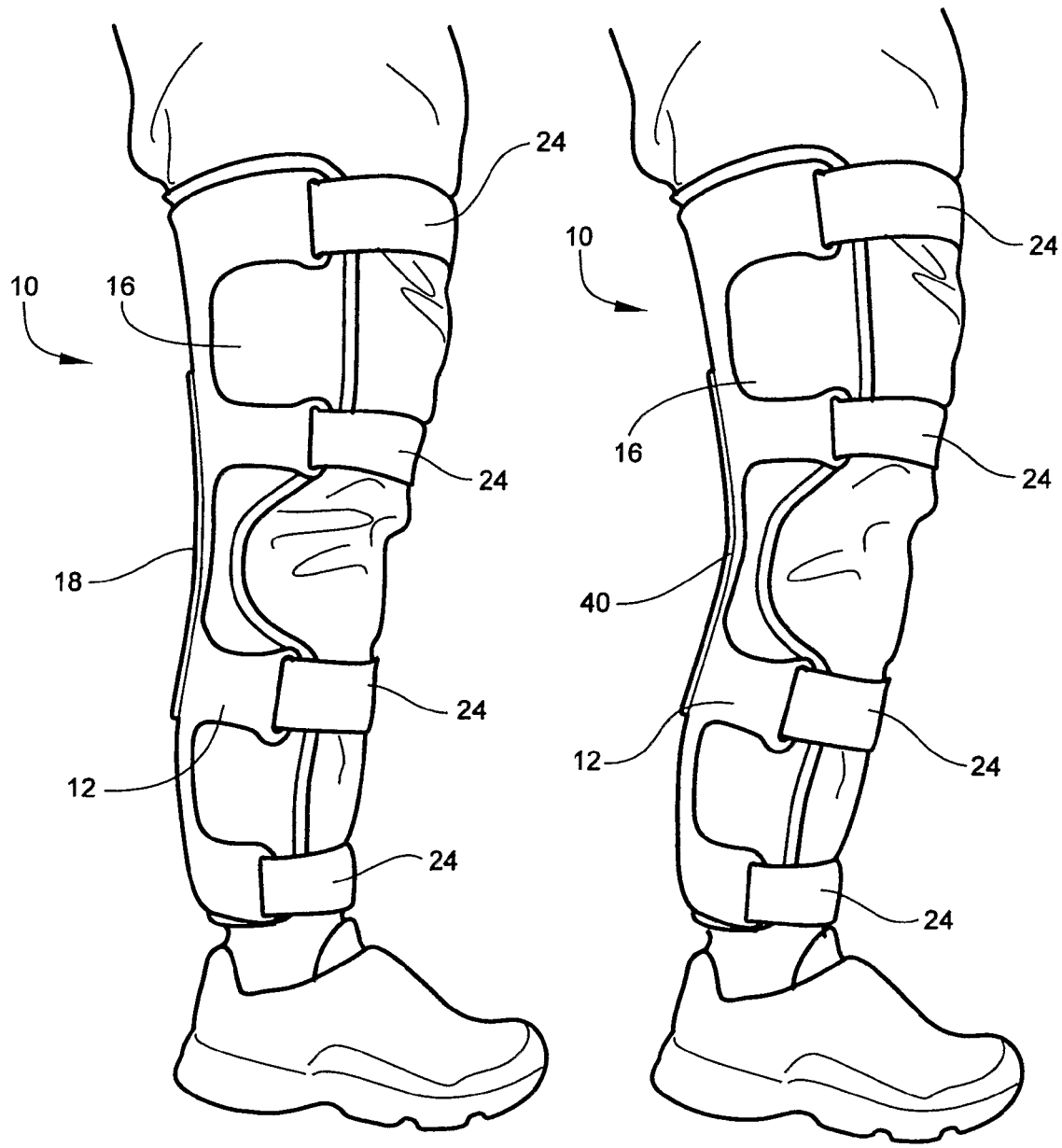
FIG. 8 is a side elevation of a knee immobilizer in place on a leg in the full extension position.
FIG. 9 is a side elevation of a knee immobilizer in place on a leg in the flexion position.

Referring now specifically to the drawings, a knee immobilizer according to the present invention is illustrated in FIGS. 1-9, and shown generally at reference numeral 10. The knee immobilizer 10 according to one preferred embodiment has four basic components, a frame 12, retainers 12A-D and 12E-H for attaching the frame to the leg, a protective, cushioning lining 16, and a spine 18 for placing and maintaining the frame in the desired position. Alternatively, and less desirably, the knee immobilizer 10 may comprise only the frame 12, retainers 12 and the spine 18, with liner formed from some other protective material separately furnished.

The frame 12 is preferably 2 mm thick polyethylene (PE 500) with a 3 mm thick, 60 mm wide reinforcement ridge extending from one end to the other along the longitudinal axis of the frame 12. The ridge may be integrally formed, applied as a separate element with adhesive, or formed by using 3 mm sheet material and grinding away material to form the 2 mm thick portions.

According to one preferred embodiment, the frame 12 is thermoformed from flat sheet material. The shape of the frame 12 may be cut from the sheet material either before of after thermoforming. According to another preferred embodiment, the frame is injection-molded of polyethylene.

Note that the frame 12 is itself relatively narrow, and contacts only the dorsal aspect of the leg. The retainers 12A-H are preferably integrally-formed with the frame 12 and are relatively narrow, extending around the lateral and medial aspects of the leg while leaving substantial intermediate open areas. These open areas, see FIGS. 8 and 9, offer reduced material requirements and weight, ease of application, enhanced comfort to the wearer. The relatively narrow width of the retainers 12A-H, on the order of approximately 50 mm, also facilitates flexibility in the circumferential direction around the leg, while permitting a much higher degree of rigidity to the integrally-formed frame 12. Preferably, the frame 12 is symmetrical left-to-right so that the knee immobilizer 10 can be used on either the left or right leg.

It has been determined that a knee immobilizer 10 having an overall proximal-to-distal length of 50 cm is adequate for most legs. Of course, larger or small sizes may be provided for very tall adults and for small adults or children, respectively. An additional 5 cm of length on the proximal end is believed to be sufficient for each the tallest adult.

The retainers 12A-H preferably include enlarged ends 20 having slots 22 therein for receiving flexible straps 24 therethrough. See FIG. 2. The straps 24 are threaded in a conventional manner through slots 22 of opposed retainers, for example, retainers 12A and 12E, and then fastened using hoop and loop members on the straps 24.

The liner 16 is preferably formed of a synthetic spacer fabric that may include, for example, velour fabric, toweling fabric, open cell foam, closed cell foam, nylon, polypropylene or other synthetic fabrics, and combinations of the above. In one particularly preferred embodiment, the liner 16 is formed of a synthetic fiber spacer fabric sold under the trademark BREATHOPRENE, laminated to a velour fabric. Preferably, the velour fabric contacts the inner, concave surface of the frame 12 and is held in position by patches 26 of hook material attached to the concave surface of the frame 12. The liner 16 may therefore be removed and replaced as needed. Alternatively, the liner 16 may be permanently attached to the frame 12, or releasably attached by other means, for example, spray, liquid or solid adhesives, double-side tape, snaps, pop rivets, or other types of touch fasteners.

As noted above, a feature of the knee immobilizer 10 is the ability to fix the angle at which the knee is immobilized by the knee immobilizer 10, even though the frame itself is relatively thin, lightweight and only semi-rigid. This is accomplished in one preferred embodiment by the spine 18. The spine 18 is preferably formed to be very rigid, and may be formed of plastic, metal, carbon fiber resin, or glass fiber, or combinations of these or similar materials. A glass-fiber/carbon fiber resin reinforced material is one suitable material from which the spine 18 may be fabricated.

In a preferred embodiment, the spine 18 is fabricated of aluminum and is attached to the frame by means of several screws 30 that are extended through holes 32 in the spine 18 and into threaded sockets 34 in the frame 12. Alternative attachment means include snaps, rivets, key and slot systems, or an aggressive touch fastener such as hermaphroditic "mushroom" or "arrow" systems.

The spine 18 shown in FIGS. 1-6 and 8 has a slight bend of about 10 degrees, which results in a full extension of the knee. In circumstances where flexion of the knee is required, as where it is desirable to lessen the strain on ligaments and tendons, a spline 40 is provided, fabricated as the spine 18, but with a bend of approximately 30 degrees, resulting in a flexion angle to the knee of approximately 20 degrees.

Alternatively, the spine can be formed from a material that can be formed to the correct angle with sufficient application of force, but which is nevertheless sufficiently rigid to maintain its angle of flexion during use.

The rigidity of the spines 18 and 40 are such that the semi-rigid frame 12 is conformed to the shape and angle of the spines 18 or 40 when the selected one is fastened and tightened onto the convex outer surface of the frame 12. The ability of the frame 12 to easily conform to the angle of the spine 18 or 40 without undue stress on the structure of the frame 12 is improved by providing a relatively more flexible zone 42 transversely-extending across the frame at the position where the bend in the spline occurs. See arrow in FIG. 7 and FIGS. 4 and 5. Preferably, the flexible zone 42 is formed by decreasing the thickness of the frame 12. However, scoring, perforations, a living hinge and coining are among the techniques that may also be suitable for providing increased flexibility.

A knee immobilizer is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

I claim:

1. A knee immobilizer, comprising:
   (a) an elongate semi-rigid frame having opposed convex and concave major surfaces for being positioned along a longitudinal axis of a dorsal aspect of a leg from above to below the knee;
   (b) a strap cooperating with the frame for encircling and retaining the frame on the leg;
   (c) a spacer lining for being positioned between the frame and the leg when in use to cushion and protect the leg against direct contact with the frame;
   (d) a first rigid spine adapted for being positioned on the frame along an elongate axis of the frame from above to below the knee in alignment with the longitudinal axis of the leg for maintaining the frame in a first predetermined rigid medical treatment extension position on the leg; and
   (e) a second rigid spine adapted for being positioned on the frame along an elongate axis of the frame from above to below the knee in alignment with the longitudinal axis of the leg for maintaining the frame in a second predetermined rigid medical treatment extension position on the leg in substitution for the first rigid spine;
   wherein the first spine is formed to an angle whereby the knee is immobilized in a position of less than 10 degrees flexion, and the second spline is formed to an angle whereby the knee is immobilized in a position of between about 10 degrees and about 30 degrees flexion.

2. A knee immobilizer according to claim 1, wherein the first and second spines are formed from one or more materials selected from the group consisting of plastic, metal, carbon fiber, and glass fiber.

3. A knee immobilizer according to claim 1, wherein the strap comprises a plurality of opposed straps integrally-formed with the frame and adapted to receive respective flexible straps for extending across a ventral aspect of the leg.

4. A knee immobilizer according to claim 1, wherein the frame is formed of a thermoplastic material.

5. A knee immobilizer according to claim 1, wherein the spacer lining is fabricated from one or more materials selected from the group consisting of velour fabric, toweling fabric, open cell foam, closed cell foam, nylon fabric, and polypropylene fabric.

6. A knee immobilizer according to claim 1, wherein the frame is symmetrical from side to side and adapted for use on both a left and right leg.

\* \* \* \* \*